United States Patent
Artsyukhovich et al.

(10) Patent No.: US 11,064,884 B2
(45) Date of Patent: Jul. 20, 2021

(54) METHOD AND APPARATUS FOR OPTICAL COHERENCE TOMOGRAPHY SCANNING

(71) Applicant: Alcon Inc., Fribourg (CH)

(72) Inventors: Alexander N. Artsyukhovich, Lake Forest, CA (US); Z. Aras Aslan, Foothill Ranch, CA (US); Hugang Ren, Pleasanton, CA (US); Lingfeng Yu, Rancho Santa Margarita, CA (US); Chengxin Zhou, Malden, MA (US)

(73) Assignee: Alcon Inc., Fribourg (CH)

( * ) Notice: Subject to any disclaimer, the term of this patent is extended or adjusted under 35 U.S.C. 154(b) by 228 days.

(21) Appl. No.: 15/874,684

(22) Filed: Jan. 18, 2018

(65) Prior Publication Data
US 2018/0199809 A1 Jul. 19, 2018

Related U.S. Application Data

(60) Provisional application No. 62/448,086, filed on Jan. 19, 2017.

(51) Int. Cl.
*A61B 3/14* (2006.01)
*A61B 3/00* (2006.01)
*A61B 3/10* (2006.01)

(52) U.S. Cl.
CPC .............. *A61B 3/14* (2013.01); *A61B 3/0025* (2013.01); *A61B 3/102* (2013.01)

(58) Field of Classification Search
CPC ......... A61B 3/14; A61B 3/102; A61B 3/0025; A61B 3/12; A61B 3/1025; A61B 3/0008;
(Continued)

(56) References Cited

U.S. PATENT DOCUMENTS 7,616,986 B2 11/2009 Seibel et al.
9,044,303 B2 6/2015 Kurtz et al.
(Continued)

FOREIGN PATENT DOCUMENTS

EP 3217144 A1 9/2017
JP 2008122295 A 5/2008
(Continued)

OTHER PUBLICATIONS

Hong et al., "Eye motion corrected OCT imaging with Lissajous scan pattern", Progress in Biomedical Society for Optical Engineering, Bellingham, WA, US, vol. 9693, Mar. 4, 2016.
(Continued)

*Primary Examiner* — William R Alexander
*Assistant Examiner* — Tamara Y. Washington (57) ABSTRACT

A method and system provide an optical coherence tomography system including a light source, an interferometric system, a processor and a memory. The interferometric system is optically coupled with the light source and includes at least one movable scanning mirror. The processor and memory are coupled with the interferometric system. The processor executes instructions stored in the memory to cause the movable scanning mirror to scan a plurality of points in a sample in at least one pattern. The at least one pattern is based on at least one of at least one Lissajous curve and at least one Spirograph curve.

4 Claims, 5 Drawing Sheets

(58) Field of Classification Search
CPC .............. A61B 3/1005; G01B 9/02091; G01B 9/02004; G01B 9/02044; G01B 9/0203; G01B 9/02035; G01B 9/02069; G01B 9/02028; G01B 2290/65; G06T 2207/30041; G06T 7/0012; G02B 21/0012; G02B 27/0093; G02B 27/0955; G02B 27/141; G02B 27/48
USPC ........................................................ 359/206
See application file for complete search history.

(56) References Cited

U.S. PATENT DOCUMENTS

| | | | |
|---|---|---|---|
| 9,066,784 B2 | 6/2015 | Goldshleger et al. | |
| 9,125,559 B2 | 9/2015 | Kersting et al. | |
| 2004/0151008 A1* | 8/2004 | Artsyukhovich | A61F 9/00817 362/572 |
| 2004/0233388 A1* | 11/2004 | Artsyukhovich | A61F 9/008 351/216 |
| 2005/0110808 A1* | 5/2005 | Goldschmidt | G09G 3/14 345/690 |
| 2005/0185192 A1* | 8/2005 | Kim | A61B 5/0066 356/497 |
| 2005/0285025 A1* | 12/2005 | Boukhny | G01L 9/0077 250/231.1 |
| 2006/0033926 A1* | 2/2006 | Artsyukhovich | G02B 26/02 356/479 |
| 2006/0103835 A1* | 5/2006 | Artsyukhovich | A61F 9/007 356/73.1 |
| 2007/0107490 A1* | 5/2007 | Artsyukhovich | A61M 1/0058 73/1.16 |
| 2007/0268720 A1* | 11/2007 | Rowe | G02B 5/001 362/572 |
| 2008/0246920 A1* | 10/2008 | Buczek | A61B 90/36 351/221 |
| 2009/0149726 A1 | 6/2009 | Hyde et al. | |
| 2010/0182569 A1* | 7/2010 | Artsyukhovich | A61B 1/0661 351/221 |
| 2011/0004149 A1* | 1/2011 | Artsyukhovich | A61F 9/00745 604/22 |
| 2011/0149592 A1* | 6/2011 | Artsyukhovich | G02B 19/0028 362/555 |
| 2013/0088414 A1 | 4/2013 | Artsyukhovich et al. | |
| 2014/0221747 A1 | 8/2014 | Tearney et al. | |
| 2015/0057524 A1 | 2/2015 | Artsyukhovich et al. | |
| 2015/0077705 A1 | 3/2015 | Artsyukhovich et al. | |
| 2015/0164311 A1 | 6/2015 | Yu et al. | |
| 2016/0128565 A1 | 5/2016 | Meznaric et al. | |
| 2017/0238798 A1 | 8/2017 | Isogai et al. | |
| 2017/0258318 A1 | 9/2017 | Wagner et al. | |

FOREIGN PATENT DOCUMENTS

| | | | |
|---|---|---|---|
| JP | 2016017915 A | * | 2/2016 |
| JP | 2016017915 A | | 2/2016 |

OTHER PUBLICATIONS

Wong et al., "In vivo imaging of human photoreceptor mosaic with wavefront sensorless adaptive optics optical coherence tomography", Biomedical Optics Express, vol. 6, No. 2, Mar. 4, 2015, pp. 580-590.

* cited by examiner

METHOD AND APPARATUS FOR OPTICAL COHERENCE TOMOGRAPHY SCANNING

BACKGROUND

Optical coherence tomography (OCT) scanning allows for non-invasive imaging of the interior of a patient's eye. A single OCT scan may provide image information into the eye (i.e. in the z-direction). In order to obtain information across the pupil (i.e. in the x-y plane), multiple scans may be performed. Typically, the images are scanned in fast x, slow y patterns. In such cases, the light beam used for OCT is scanned rapidly across the eye in the x direction, moving in the y direction slightly after each scan. Thus, such a pattern is effectively a zigzag. Fast y, slow x patterns might also be used. Other possible patterns are a spiral from the pupil outwards or vice versa. Similarly, a circular patterns with varying diameters might also be used to scan the patient's eye. Multiple scans may be concatenated to provide a three-dimensional image of the eye.

Although such mechanisms allow for non-invasive imaging of the interior of the eye, there may be issues in the data obtained, time taken to complete the OCT scans and/or the longevity of the OCT system. Fast x, slow y and the fast y, slow x scans and circular patterns place high stress on the mirror(s) used to direct the light at the patient's eye. Consequently, portion(s) of the OCT system, particularly those related to scanning mirror(s), may malfunction or fail. In addition, some scan patterns, such as a spiral scan, take a relatively long time to complete. Because the patient's eye may move during the pattern, registration errors are more likely to occur during longer scan patterns. As a result, the OCT image may be less reliable.

Accordingly, there is a need for improved OCT scanning techniques that reduce stress on OCT system components while keeping scan times short.

SUMMARY

In certain embodiments, a method and system provide an optical coherence tomography system including a light source, an interferometric system, a processor and a memory. The interferometric system is optically coupled with the light source and includes at least one movable scanning mirror. The processor and memory are coupled with the interferometric system. The processor executes instructions stored in the memory to cause the movable scanning mirror to scan a plurality of points in a sample in at least one pattern. The at least one pattern includes at least one of at least one Lissajous curve and at least one Spirograph curve.

In some embodiments, the at least one pattern is the at least one Lissajous curve. The Lissajous curve may have a plurality of x values proportional to a first plurality of values for $\sin(mt+\delta)$ and a plurality of y values proportional to a second plurality of values for $\sin(nt)$. In such an embodiment, m and n are constant parameters, the ratio m/n is ≤10, t varies, and $\delta$ is a nonzero constant. In some embodiments, m/n is ≤2. In some cases, the at least one pattern is the at least one Spirograph curve. The Spirograph curve may have a plurality of x values proportional to a first plurality of values for $(R+r)\cos(t)+p^*\cos((R+r)t/r)$ and a plurality of y values proportional to a second plurality of values for $(R+r)\sin(t)+p^*\sin((R+r)t/r)$. In such an embodiment, R, r and p are constant parameters and t varies. In such an embodiment, the scanning mirror(s) includes a first mirror, a second mirror and a third mirror. The first mirror has at least a first reflected surface oriented at an acute angle. The second mirror has a second reflective surface facing and parallel to a third reflective surface of the third mirror.

The processor may execute instructions stored in memory to cause the movable mirror(s) to scan a first portion of the plurality of points in the sample according to a first pattern based on a first Lissajous curve. The processor may also cause the movable mirror(s) to scan a second portion of the plurality of points in the sample according to a second pattern based on a second Lissajous curve. In other embodiments, the processor may execute instructions stored in memory to cause the movable mirror(s) to scan a first portion of the plurality of points in the sample according to a first pattern based on a Lissajous curve. The processor may also cause the movable mirror(s) to scan a second portion of the plurality of points in the sample according to a second pattern based on a Spirograph curve. In still other embodiments, the processor may execute instructions stored in memory to cause the movable mirror(s) to scan a first portion of the plurality of points in the sample according to a first pattern based on a first Spirograph curve. The processor may also cause the movable mirror(s) to scan a second portion of the plurality of points in the sample according to a second pattern based on a second Spirograph curve. In each of these embodiments, the moveable mirror(s) may switch from the first pattern to the second pattern at a location where the first and second patterns overlap.

In some embodiments, the processor executes instructions stored in memory to scan the plurality of points a plurality of times in a refresh time of less than one second. In some such embodiments, the refresh time is not more than five hundred milliseconds and the plurality of times is at least ten times. In some cases, the refresh time is not more than one hundred milliseconds.

In another aspect, a method for diagnosing an ophthalmic condition in an eye of a patient using an optical coherence tomography (OCT) system is described. The method includes scanning a plurality of points in the eye according to at least one pattern. The at least one pattern is selected from at least one Lissajous curve and at least one Spirograph curve. The scanning step is repeated a plurality of times within a refresh time that is less than one second. The refresh time may be not more than five hundred milliseconds. In some cases, the refresh time is not more than one hundred milliseconds.

In some embodiments, the at least one Lissajous curve has a first plurality of x values proportional to a first plurality of values for $\sin(mt+\delta)$ and a first plurality of y values being proportional to a second plurality of values for $\sin(nt)$. In such an embodiment, m and n are numbers, the ratio m/n is less than or equal to 10, t varies, $\delta$ is a nonzero constant and m is different from n. In some cases, the ratio m/n is less than or equal to 2. For example, the ratio m/n may be less than or equal to 1. In some embodiments, the at least one Spirograph curve has a first plurality of x values proportional to a second plurality of values for $(R+r)\cos(t)+p^*\cos((R+r)t/r)$ and a first plurality of y values proportional to a third plurality of values in $(R+r)\sin(t)+p^*\sin((R+r)t/r)$. In such an embodiment, R, r and p are constant parameters and t varies.

In some embodiments, the scanning step includes scanning a first portion of the plurality of points in the eye according to a first pattern based on a first Lissajous curve; and scanning a second portion of the plurality of points in the eye according to a second pattern based on a second Lissajous curve. In other cases, the scanning step includes scanning a first portion of the plurality of points in the eye according to a first pattern based on a first Lissajous curve and scanning a second portion of the plurality of points in the eye according to a second pattern based on a Spirograph curve. In some embodiments, the scanning step includes scanning a first portion of the plurality of points in the eye according to a first pattern based on a first Lissajous curve and scanning a second portion of the plurality of points in the eye according to a second pattern based on a Spirograph curve. In all such embodiments, the first scan pattern is switched to the second scan pattern at a location where the first and second patterns overlap.

The methods and systems disclosed herein may provide one or more advantages. For example, certain embodiments allow the pupil of a patient to be rapidly and reliably scanned with reduced mechanical stress on the mirror(s) of the OCT system. Other advantages and benefits are discussed below, and others will be apparent to a skilled artisan in view of the drawings and specification.

DETAILED DESCRIPTION

The exemplary embodiments relate to systems and methods for performing optical coherence tomography (OCT), for example to image the interior of the eye. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein. The method and system are also described in terms of singular items rather than plural items. For example, a pattern and/or a single scan is used and/or shown in some embodiments. One of ordinary skill in the art will recognize that these singular terms encompass plural. For example, multiple scans may be performed and/or systems or components might be used.

In certain embodiments, the system includes one or more processors and a memory. The one or more processors may be configured to execute instructions stored in the memory to cause and control some or all of the process(es) set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of hardware, software (including firmware, resident software, micro-code, etc.) or a combination of software and hardware aspects. Furthermore, aspects of the method and system may take the form of a software component(s) stored in memory and executed by at least one processor. Software may be embodied in one or more computer readable medium(s) having computer readable program code embodied thereon. As used in the claims, the terms "processor," "memory," and "instructions" each refers to a classes of structures known in the field of OCT imaging and familiar to those of ordinary skill in the art. Accordingly, these terms are to be understood as denoting structural rather than functional elements of the disclosure.

Figure 1:
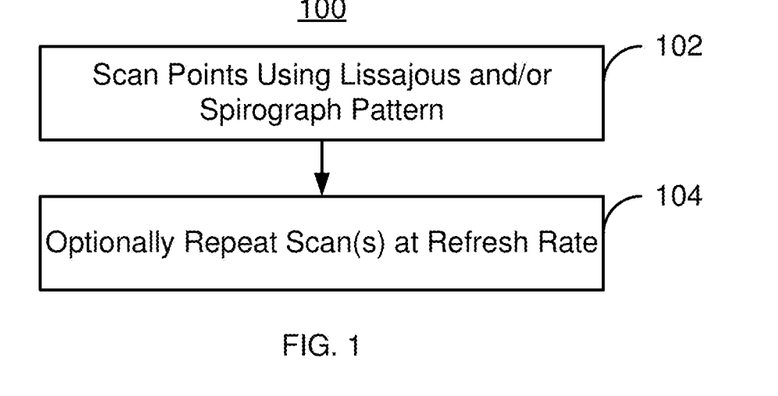
FIG. 1 is a flow chart depicting an exemplary embodiment of a method for performing an OCT scan.

FIG. 1 is a flow chart depicting an exemplary embodiment of a method 100 for performing OCT scan(s) according to the disclosure. For simplicity, some steps may be omitted, interleaved, performed in another order and/or combined. The method 100 may be implemented by a processor of an OCT system controller executing instructions stored in memory to control various portions of a spectral-domain OCT (SD-OCT) or swept-source OCT (SS-OCT) imaging system.

Figure 2A:
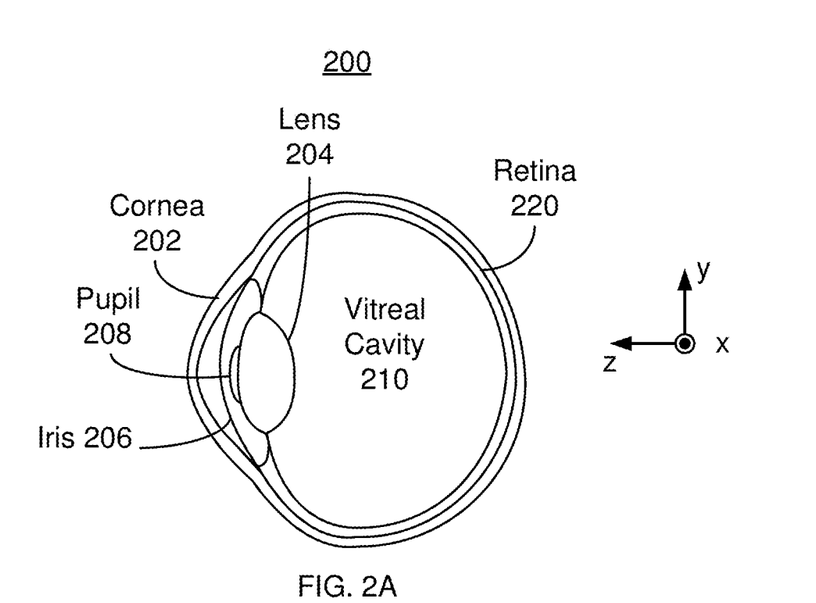
FIGS. 2A-2B are diagrams depicting an eye that may be scanned using OCT and a scan pattern superimposed on a pupil.
Figure 2B:
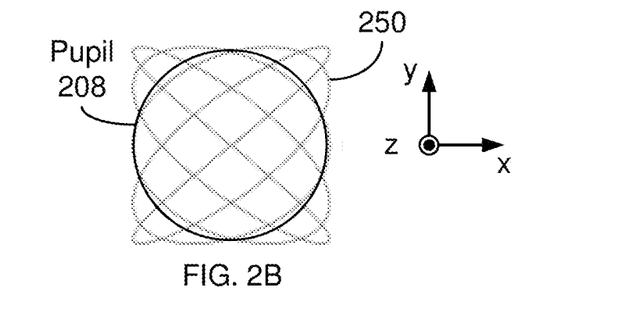

FIGS. 2A-2B are diagrams depicting an eye. In particular, FIG. 2A depicts a cross-sectional view of the eye that may be scanned using the method 100. The cornea 202, lens 204, iris 206, pupil 208, vitreal cavity 210 and retina 220 are indicated for the purposes of explanation. FIG. 2B is a plan view of the eye 200 that may be scanned using the method 100. In particular, FIG. 2B depicts an example scan pattern superimposed on a portion of the eye. The method 100 is described in the context of performing an OCT imaging procedure on the eye 200. However, the method 100 may be extended to other samples as well.

In general, the components of such OCT imaging systems are well-known to the skilled artisan. To aid understanding, aspects of an example OCT imaging system (e.g., the systems 100 and 150 depicted in FIGS. 6 and 7) are described below, but it should be understood that OCT systems according to the disclosure include additional features and components that are not addressed here for brevity.

According to method 100, an OCT system scans an OCT imaging beam to points of a target using one or more Lissajous and/or Spirograph patterns at step 102. In this example, an OCT A-scan may executed at various points in a scan pattern to obtain data that is a few microns into the interior of the eye (i.e. in the negative z-direction from the pupil). The scan used in step 102 is in or parallel to the x-y plane. Thus, samples at a particular z-depth may be obtained. The samples at this z-depth may be taken in the Lissajous or Spirograph patterns. Alternatively, the scans may have different z-depths.

In some embodiments, an OCT system scans an OCT imaging beam according to a scan pattern based on a Lissajous curve. A Lissajous curve may be generally described as having x values that are proportional to $\sin(nt)$ and y values that are proportional to $\sin(mt+\delta)$, where m is a nonzero constant, n is a nonzero constant, t varies and $\delta$ is a nonzero phase delay such as $\pi/2$. Different Lissajous curves may be obtained for different values of n and m, as the ratio of m/n modifies characteristics of the Lissajous curve. Accordingly, n and m may be integers or any other real numbers. In certain embodiments, the ratio of $m/n \leq 10$. In other embodiments: $m/n \leq 8$, $m/n \leq 6$, $m/n \leq 4$, $m/n \leq 2$, or $m/n \leq 1.5$. Values for different scan patterns based on Lissajous curves may be calculated and stored in lookup tables in memory accessed by a processor of the OCT system.

FIG. 2B depicts an example Lissajous curve 250 which may be used to scan the eye 200. In FIG. 2B, the Lissajous curve 250 is superimposed on the pupil 208. Because of the shape of the Lissajous curve 250, data may be taken at multiple points that cover the pupil 208.

Figure 3A:
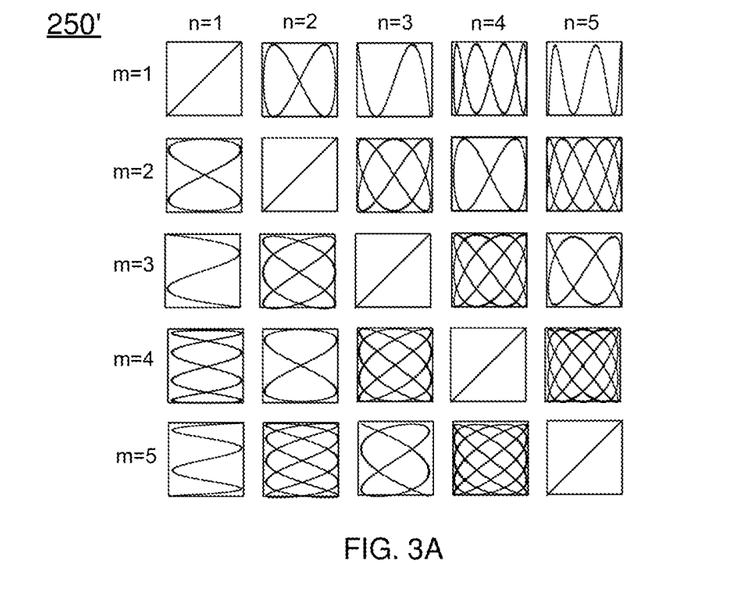
FIGS. 3A-3C are diagrams depicting example Lissajous patterns that may be used as scan patterns for OCT and particular Lissajous scan patterns superimposed on a pupil.
Figure 3B:
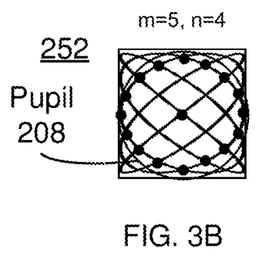
Figure 3C:
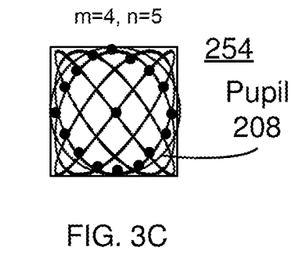

FIGS. 3A-3C depict examples of other Lissajous curves. For example, FIG. 3A depicts various Lissajous curves 250' for different exemplary values of m and n. In particular, the value of n increases from 1 to 5 moving across the columns of FIG. 3A from left to right. Similarly, the value of m increases from 1 to 5, moving down each row from top to bottom. Accordingly, FIG. 3A depicts how the Lissajous curve changes as the ratio of m/n is modified. Moreover, as illustrated by the Lissajous curves 250', if a Lissajous pattern is scanned in step 102, then the center of the pupil will be scanned in all cases (provided the OCT system and pupil are correctly aligned).

FIGS. 3B and 3C depict scan patterns 252 and 254 based on Lissajous curves for m=5, n=4 (row 5, column 4 of FIG. 3A) and m=4, n=5 (row 4, column 5 of FIG. 3A), respectively. The pupil 208 is also shown. As illustrated in FIGS. 3B and 3C, scanning pupil 208 according to Lissajous patterns 252 and 254 may cover or provide representative scan points across most or all of the area of the pupil 208, including the center. Moreover, patterns 252 and 254 are mirror images of one another. In some embodiments an OCT scanner may switch from pattern 252 to pattern 254 during an OCT imaging procedure at a point where the patterns intersect or overlap. These intersection points are indicated by darkened circles in FIGS. 3B and 3C. Switching between patterns 252 and 254 at such intersection points may allow for reduced stress on OCT scanner mirror(s) (not shown in FIGS. 3A-3C) used to perform method 100. For example, if x and y scanners are operating separately at their own resonant frequencies (e.g., x at 8 kHz and y at 10 kHz), and if the initial phase difference is constant, then the stress difference between scan patterns 252 and 254 should be minimal or zero. Further, switching between patterns 252 and 254 allows the slight asymmetry of each pattern to be compensated. Moreover, the outer intersection points shown in FIGS. 3A and 3B approximate a circle, and the patterns 252 and 254 may be sized such that the circles formed by each correspond to the outer circumference of the pupil 208. Thus, step 102 may utilize multiple patterns for a single imaging procedure.

In some embodiments, an OCT system scans an OCT imaging beam in step 102 according to a scan pattern based on a Spirograph curve. One example of a Spirograph curve has x that are proportional to $(R+r)\cos(t)+p^*\cos((R+r)t/r)$ and y values that are proportional to $(R+r)\sin(t)+p^*\sin((R+r)t/r)$ where R, r and p are constant parameters and t varies. Values for different scan patterns based on Spirograph curves may be calculated and stored in lookup tables in memory accessed by a processor of the OCT system.

Figure 4:
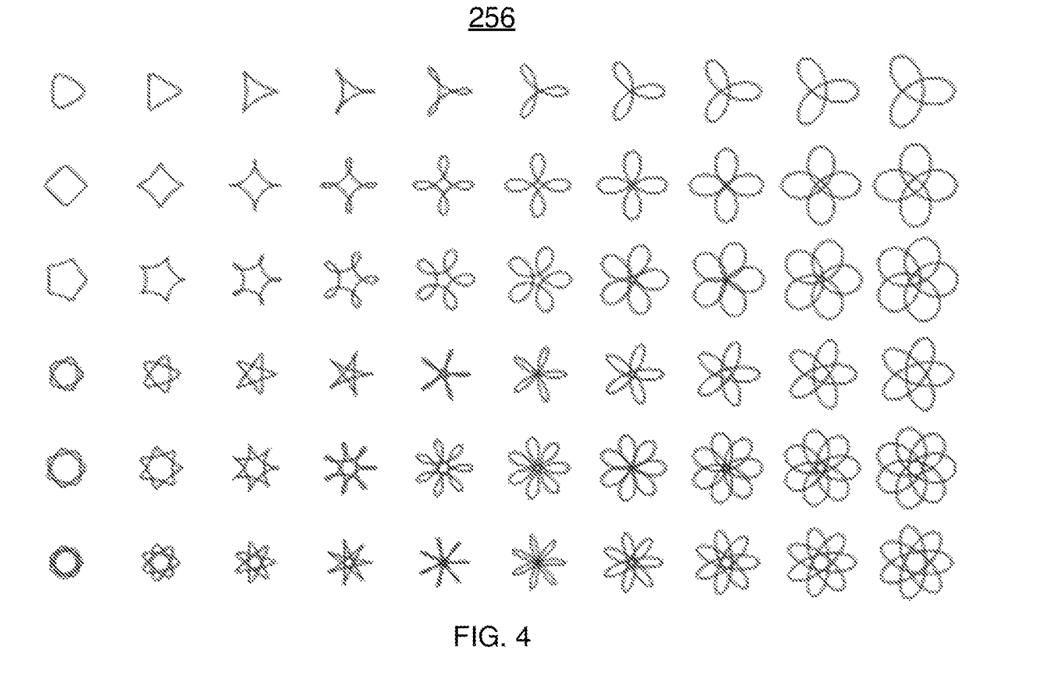
FIG. 4 is a diagram depicting example Spirograph patterns that may be used as scan patterns for OCT.

FIG. 4 depicts various Spirograph patterns 256. Note that if an OCT system scans according to a Spirograph pattern in step 102, then the center of the eye will not be scanned in any example. Moreover, Spirograph patterns 256 are all radially symmetric, and may take various forms according to other equations which will be apparent to those skilled in the art. As discussed above with respect to the Lissajous patterns 252 and 254, the OCT system may switch between various Spirograph patterns at locations in which the patterns intersect, or overlap. Similarly, the OCT system may switch between Spirograph and Lissajous patterns, between Spirograph and other patterns, and/or between Lissajous and other patterns. Switching between patterns may occur at locations where the patterns overlap. Thus, step 102 is not limited to a single pattern for an imaging procedure.

It is noted that, although a particular mathematical description of Lissajous curves and Spirograph patterns are described herein by particular equations, one skilled in the art will appreciate that such curves and patterns are not limited to the example equations set forth herein. Rather, Lissajous curves and Spirograph patterns may be expressed in various mathematically analogous or equivalent equations. Accordingly, the scope of the disclosure is not limited to the particular expressions set forth herein, but generally includes Lissajous and Spirograph patterns consistent with the principles of the disclosure.

Referring to FIGS. 1-4, the scanning step 102 may optionally be repeated a sufficient number of times to obtain data for the desired region within a refresh time, at step 104. This refresh time may be less than one second. In some embodiments, the refresh time is not more than 500 milliseconds. In some such embodiments, the refresh time is not more than one hundred milliseconds. For example, a 100 kHz laser may be used as a light source and the frequency with which the laser may be scanned may be 10 kHz. The method 100 might use 1-1000 scans to obtain data for the desired number of points across the desired area of the eye. In some embodiments, approximately 10 scans are performed in order to provide the data. This number of scans may be performed in 0.01 seconds (100 milliseconds) or less. Thus, the method 100 may refresh the pattern in a refresh time of not more than 100 milliseconds. Accordingly, certain embodiments can scan according to a Lissajous pattern faster than saccadic eye movements. As a result, the eye may be considered motionless during Lissajous scanning according to certain embodiments, which may be particularly useful for intra-operative aberrometry integrated with OCT.

Thus, using the method 100, an OCT system may generate OCT images using one or more Lissajous and/or Spirograph scan patterns. Use of these patterns may result in various benefits. Lissajous and Spirograph patterns may cover or provide representative scan points across most or all of the area of the pupil in fewer scans. For example, sufficient data may be obtained using at least five and not more than ten scans. These scans may also be faster and, therefore, completed more rapidly. For example, the five through ten scans mentioned above may be completed in a refresh time on the order of five hundred milliseconds or less. In some cases, this refresh time is not more than one hundred milliseconds. The Lissajous and Spirograph patterns may also have axial symmetry and/or partial rotational symmetry. Further, Lissajous and Spirograph patterns provide additional stability against registration errors because fewer scans may cover (or provide representative scan points across) the entire area of the pupil. In addition, these patterns may be suitable for ophthalmic instrument and eye tracking as well as for ocular biometry. For example, the radii of curvature and locations of the major eye structures such as the cornea, lens and retina may be determined. The use of Lissajous and Spirograph patterns may also put reduced mechanical stress on the system. Thus, the OCT system used with the method may be more reliable and have a longer lifetime. A single scan may be completed in less than five milliseconds, which is faster than saccadic eye movements. The patterns may be used in applications such as intra-operative aberrometry. For Lissajous patterns, the center of the eye may always be scanned. Thus, if the center of the eye is of interest, Lissajous patterns may be particularly useful. In contrast, Spirograph patterns do not scan the center of the eye. Consequently, Spirograph patterns may be of particular utility if the center of the eye is desired to be omitted, for example because of artifacts in the data. As a result, OCT may be better performed using the method 100.

Figure 5:
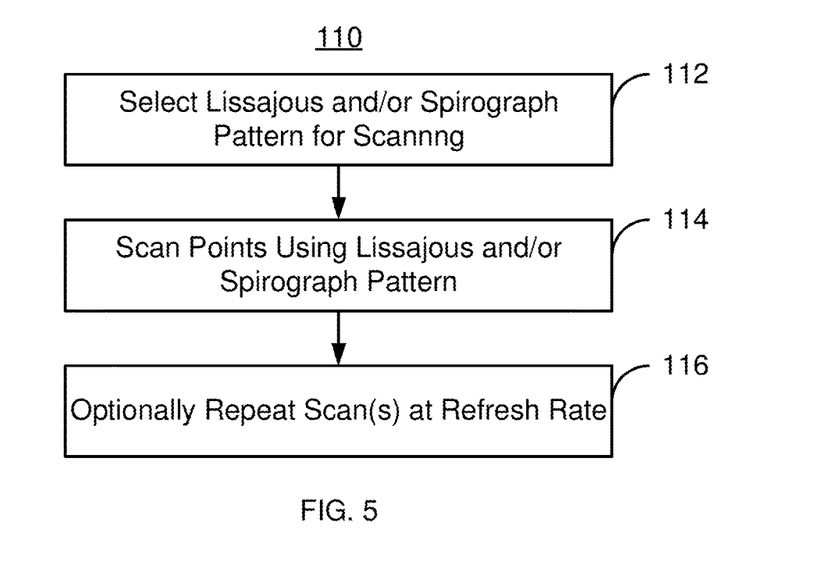
FIG. 5 is a flow chart depicting another exemplary embodiment of a method for performing an OCT scan.

FIG. 5 is a flow chart depicting an exemplary embodiment of a method 110 for performing OCT scan(s). For simplicity, some steps may be omitted, interleaved, performed in another order and/or combined. The method 110 may be performed by a processor of an OCT system controller executing instructions stored in memory to control various portions of a spectral-domain OCT (SD-OCT) or swept-source OCT (SS-OCT) imaging system.

Figure 6:
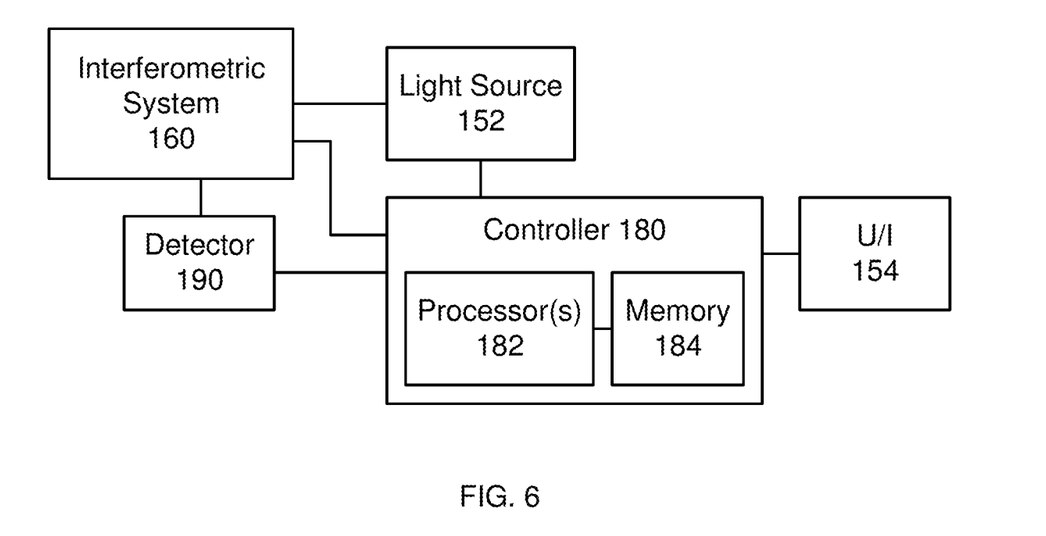
FIG. 6 is a diagram depicting an exemplary embodiment of a system for performing OCT scans using Lissajous and/or Spirograph patterns.
Figure 7:
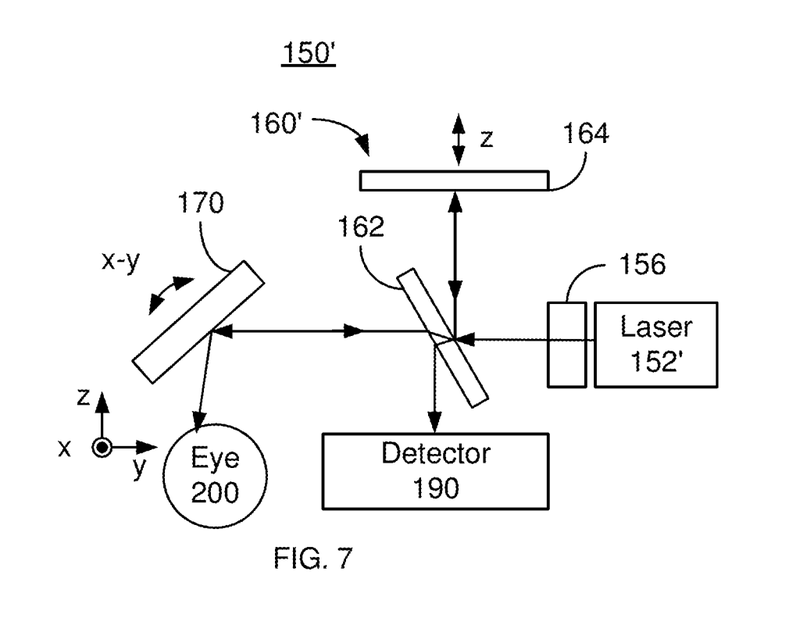
FIG. 7 is a diagram depicting another exemplary embodiment of a portion of a system for performing OCT scans using Lissajous and/or Spirograph patterns.

FIGS. 6 and 7 depict aspects of an example OCT system 150/150' that may perform some or all of the steps of methods 100 and 110. In particular, FIG. 6 illustrates functional blocks of OCT system 150, and FIG. 7 depicts the structure of particular aspects of system 150'. It should be understood that systems 150 and 150' are complimentary depictions of an example SD-OCT or SS-OCT imaging system. Consequently, like or related components have like labels.

FIG. 6 is a functional diagram of OCT system 150 which includes a light source 152, a user interface (U/I) 154, an interferometric system 160 (which includes a beam splitter/combiner 162, adjustable reference mirror 164, and a scanner), an OCT controller 180 (which includes a processor configured to execute instructions stored in memory) and a detector 190. For simplicity, only certain components of the OCT system 150 are shown.

The light source 152 may comprise any suitable low-coherence light source such as a super-luminescent diode, ultrashort (e.g., femtosecond) pulsed laser, or supercontinuum laser, and may comprise a frequency-swept or tunable laser in certain examples, such as SS-OCT systems. The beam splitter/combiner 162 may comprise a non-polarized beam splitter for splitting the OCT beam into an imaging beam and a reference beam and combining or directing reflected imaging and reference light toward a reference mirror 164 which can be adjusted to calibrate the depth of the OCT image. The scanner may comprise one or more galvanometer-controlled mirrors (e.g., movable mirror(s) 170, 170') to scan the imaging beam in the x-y plane toward a target or sample, such as the cornea or retina of an eye. A scanner may additionally or alternatively comprise other components, such as microelectromechanical systems (MEMS) or a resonant scanner. The imaging beam scanned by the scanner is directed through optical elements which may comprise focusing and/or collimating lenses (not shown). Detector 109 receives the imaging beam reflected from the target and the reference beam reflected from the reflector and outputs an interference signal from which an OCT image can be generated. The interferometer may include any suitable combination of spectrometers, photo-detectors, array detectors, analog-to-digital converters (ADCs), diffraction grating(s), or other components known to those skilled in the art. For example, in an SD-OCT system the interferometer may include a diffraction grating, lenses, and an array detector such as a charge-coupled device (CCD). In an SS-OCT system, the interferometer may include a photodetector and an analog-to-digital converter.

An OCT controller 180 comprising hardware, firmware, and software configured to control components of the OCT system (such as the scanner) to acquire and display OCT images of a target. Controller 180 includes one or more processors 182 configured to execute instructions stored in memory 184. User interface 154 may include one or more displays to present OCT images generated by the OCT controller, control menus, and the like. In various examples, the display may include any one or more monitors, projectors, oculars, heads-up displays, screens, glasses, goggles, etc. The OCT images may be displayed as 2D or 3D images. User inputs may be received by user interface 154 via keyboard, mouse, touchscreen, gesture recognition system, and any other suitable input.

FIG. 7 depicts structural aspects of OCT system 150' that may perform the methods 100 and/or 100'. For simplicity, only certain components of the OCT system 150' are shown. The OCT system 150' provides a complimentary view of the OCT system 150, and related or same components have similar labels. The OCT system 150' illustrated in FIG. 7 includes light source 152', interferometric system 160' and detector 190 that are analogous to the light source 152, interferometric system 160 and detector 190, respectively, of FIG. 6. Other portions of the OCT system 150' are omitted for clarity. Also shown is the eye 200 being imaged by the OCT system 150'. The light source 152' is explicitly shown as a laser.

OCT system 150' includes a light source 152, which may be a pulsed laser, and may include a collimator 156. The interferometric system 160' includes beam splitter/combiner 162, reference mirror 164, and scanning mirror(s) 170. The position of mirror 164 is adjusted to set the path length of the OCT reference beam, thereby controlling the depth at which samples for the OCT scan are taken (the z-direction). The scanning mirror(s) 170 are used to control scanning of the OCT imaging beam across the eye 200 (scans within planes parallel to the x-y plane). Thus, the scanning mirror(s) 170 (directed by signals from OCT controller 180) may be used to scan the eye 200 in Lissajous and/or Spirograph patterns. Although one mirror 170 is shown in FIG. 7, multiple mirrors may be used.

In operation, light from the laser 152' traverses the collimator 156 and split by the beam splitter 162. Reference light is provided to the mirror(s) 164. This light is reflected back to the beam splitter 162 and provided to the detector 190. The remaining portion ("investigative light") is provided to the scanning mirror(s) 170, which direct the investigative light to the desired portion of the eye 200. A portion of this investigative light is scattered off of structures within the eye 200 and returned back to the mirror(s) 170. This scattered light is reflected back to the beam splitter 162 and provided to the detector 190. The reference light and investigative/scattered light may be processed and compared to generate an OCT image.

Additionally, some embodiments of systems 150 and 150' may include an aberrometry laser. For example, in examples of system 150' a laser beam generated by an aberrometry laser may be combined with an OCT imaging beam by a beam splitter located between beam splitter 162 and scanner 170. Such a beam splitter 162 may include special cutoff filtering properties. For example, light source 152' may be configured to generate an OCT laser beam of at least 1000 nm. System 150' may further include an aberrometry laser source (not shown) configured to generate an aberrometry laser beam of no more than 800 nm. A beam splitter configured to transmit near 100% of light above 900 nm and near 0% of light below 900 nm may be located between beam splitter 162 and scanner 170. Accordingly, the aberrometry laser may transmit the aberrometry laser beam toward this beam splitter, which will reflect the aberrometry laser beam into the beam path of the OCT laser beam it transmits, thereby combining the beams. In this manner, the aberrometry laser may be activated at particular points in the scan pattern to produce an aberrometry pattern that can be interpreted for refractive analysis of the eye 200.

Returning to FIG. 5, method 100' is described in the context of and may be performed using the example OCT system 150/150'. Steps of method 110 may be implemented by a processor of an OCT system controller executing instructions stored in memory to control various portions of a spectral-domain OCT (SD-OCT) or swept-source OCT (SS-OCT) imaging system. However, the method 100' may be used with other apparatus and the OCT system 150 may be used with another method.

At step 112, one or more scan pattern(s) are selected for use in OCT scans. Step 112 may include receiving a user selection for one or more patterns via a user interface. Alternatively, default or other pattern(s) may be automatically selected by a processor executing instructions stored in memory of an OCT controller 180. The pattern(s) selected include one or more Lissajous curves (e.g., 250, 250', 252, 254, etc.) and/or one or more Spirograph curves (e.g., 256).

Various points in the eye are scanned using the selected pattern(s) at step 114. Step 114 is analogous to step 102 of the method 100. Thus, the OCT controller 180 controls a scanner (e.g., scanning mirror(s) 170) to direct light from the light source 152 to various points in the eye from which data may be obtained. The light is directed at locations using the pattern(s) selected in step 112. If multiple patterns are to be used, then it is desirable for the OCT system 150/150' to switch between patterns at locations at which the patterns overlap. The detector 190 detects OCT light reflected from the eye and interferes it with OCT light reflected by the reference mirror 164. Thus, data for locations in Lissajous and/or Spirograph patterns at a particular depth may be collected. Multiple scans may be taken at different depths or a single scan may collect data at multiple depths by adjusting the position of reference mirror 160'. In some embodiments, the detector 190 provides the data to the OCT controller 180 for further processing. In other embodiments, another component may process the data separately or in conjunction with the controller 180.

The scanning step 114 may optionally be repeated to obtain data for the desired region within a refresh time, at step 116. Step 116 is analogous to step 104. Step 116 may also include providing the data to the user via the U/I 154. For example, the data may be used to provide an OCT scan on a display.

Using the method 110/110' and OCT system 150/150', OCT imaging may be performed using Lissajous and/or Spirograph scan patterns. Use of these patterns may result in various benefits. For example, Lissajous and Spirograph patterns may cover the entire area of the pupil (or yield representative scans across the pupil) in fewer scans. These scans may also be faster and, therefore, completed more rapidly. In addition, the method 110/110' and OCT system 150/150' provide stability against registration errors because fewer scans may cover the entire pupil. The Lissajous and Spirograph patterns may also have axial partial rotational symmetry. Ophthalmic instrument and eye tracking as well as ocular biometry may also be performed. The method 110/110' may also have reduced mechanical stress on the OCT system 150/150', including in particular the scanner mirror(s) 170. Thus, the mirror 170 and OCT system 150' may thus be less likely to wear and break. The OCT system 150/150' may be more reliable and have a longer lifetime. Moreover, the patterns may be used for intra-operative aberrometry. Depending upon the pattern selected, the center of the eye may be scanned or omitted. As a result, OCT may be better performed using the method 110/110' and OCT system 150/150'.

Figure 8:
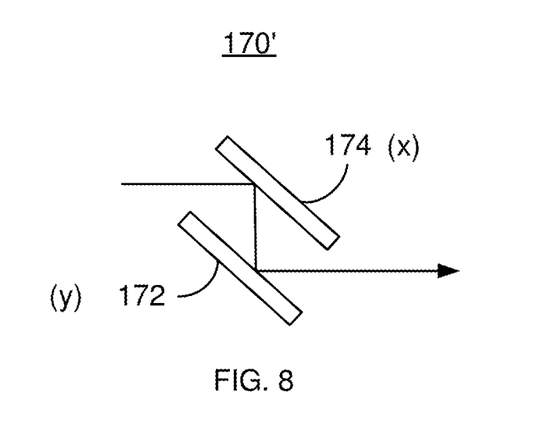
FIG. 8 is a diagram depicting an exemplary embodiment of a portion of a system for performing OCT scans using Lissajous and/or Spirograph patterns via a galvo scanner.

FIG. 8 is a diagram depicting another exemplary embodiment of a portion of an OCT system that performs scans using Lissajous patterns via a galvo X-Y scanner. In particular, mirrors 170' are shown. It is noted that mirror(s) 170 of FIG. 7 may comprise mirrors 170' as shown in FIG. 8. In particular, two mirrors 172 and 174 are shown. The mirrors 172 and 174 are parallel and separated by a particular distance. Thus, one mirror 172 may be used to control the y value of the location being scanned. The other mirror 174 may be used to control the x value of the location being scanned. The distance between the mirrors 172 and 174 may be desired to be small to reduce distortions in the patterns being scanned.

An OCT system 150/150' using the mirrors 170' may share the benefits of the systems and methods described above. In addition, each mirror 172 and 174 may be operated separately. Thus, the various Lissajous patterns 250 may be used for scanning without varying the stresses exerted on the mirrors 172 and 174. For example, scanning according to the m=4, n=5 Lissajous pattern described above may effectively impose the same stress on mirrors 170 and 174 as scanning according to the m=5, n=4 Lissajous pattern.

Figure 9:
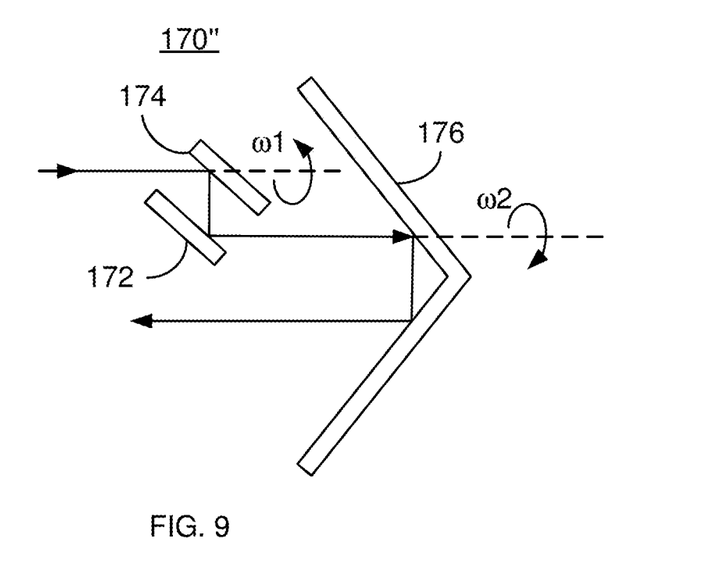
FIG. 9 is a diagram depicting an exemplary embodiment of a portion of a system for performing OCT scans using Lissajous and/or Spirograph patterns.

FIG. 9 is a diagram depicting another exemplary embodiment of a portion of an OCT system 150/150' that performs scans using Spirograph patterns. In particular, mirrors 170" are shown. It is noted that mirror(s) 170 of FIG. 7 may comprise mirrors 170' depicted in FIG. 8. In particular, three mirrors 172, 174 and 176 are shown in FIG. 9. The mirrors 172 and 174 are analogous to those shown in FIG. 8. The mirrors 172 and 174 are parallel and separated by a particular distance. Also shown is scanning mirror 176 having reflective surfaces that are oriented at a nonzero angle. In the embodiment shown, the reflective surfaces are substantially orthogonal. In order to scan the Spirograph pattern, the mirrors 172 and 174 are configured to rotate with a first angular frequency, $\omega 1$, around the axis shown. In another embodiments, an axis different from the input laser beam may be used. The second mirror 176 is configured to rotate around the axis shown with a second angular frequency, $\omega 2$. The first and second angular frequencies are selected to provide the Spirograph pattern in the time desired. The desired Spirograph pattern may be provided using the mirrors 170". Thus, an OCT system using the mirrors 170" may share the benefits of the systems and methods described above.

Methods and systems for providing OCT scans have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. An optical coherence tomography (OCT) system comprising:

a light source;

an interferometric system optically coupled with the light source and comprising a first mirror, a second mirror and a third mirror, the first mirror having at least a first reflected surface oriented at an acute angle, the second mirror having a second reflective surface facing and parallel to a third reflective surface of the third mirror; and a processor and memory coupled with the interferometric system, the processor executing instructions stored in the memory to cause the at least one movable scanning mirror to scan a plurality of points in a sample according to at least one pattern, the at least one pattern based on at least one of a Lissajous curve and a Spirograph curve;

wherein the processor executes instructions stored in memory to:

cause the at least one movable scanning mirror to scan a first portion of the plurality of points in the sample according to a first pattern based on a first Lissajous curve;

cause the at least one movable scanning mirror to scan a second portion of the plurality of points in the sample according to a second pattern based on a second Lissajous curve; and switch from the first pattern to the second pattern at a location where the first and second patterns overlap.

2. The OCT system of claim 1 wherein the processor executes instructions stored in memory to scan the plurality of points a plurality of times in a refresh time of less than one second.

3. The OCT system of claim 2 wherein the refresh time is not more than five hundred milliseconds and the plurality of times is at least ten times.

4. The OCT system of claim 1, further comprising:

wherein the refresh time is not more than one hundred milliseconds.

* * * * *